(12) United States Patent
Allain et al.

(10) Patent No.: US 8,848,989 B2
(45) Date of Patent: Sep. 30, 2014

(54) CARDIAC IMAGE PROCESSING AND ANALYSIS

(75) Inventors: Pascal Allain, Saint Cyr Lecole (FR); Sherif Makram-Ebeid, Dampierre (FR); Oudom Somphone, Antony (FR)

(73) Assignee: Koninklijke Philips N.V., Eindhoven (NL)

( * ) Notice: Subject to any disclaimer, the term of this patent is extended or adjusted under 35 U.S.C. 154(b) by 245 days.

(21) Appl. No.: 13/145,920

(22) PCT Filed: Jan. 18, 2010

(86) PCT No.: PCT/IB2010/050210
§ 371 (c)(1),
(2), (4) Date: Jul. 22, 2011

(87) PCT Pub. No.: WO2010/084446
PCT Pub. Date: Jul. 29, 2010

(65) Prior Publication Data
US 2011/0274326 A1    Nov. 10, 2011

(30) Foreign Application Priority Data

Jan. 23, 2009   (EP) .................................... 09305062

(51) Int. Cl.
*G06K 9/00*     (2006.01)
*G06T 7/00*     (2006.01)
*A61B 6/00*     (2006.01)
*A61B 8/08*     (2006.01)

(52) U.S. Cl.
CPC ......... *A61B 8/08* (2013.01); *G06T 2207/30048* (2013.01); *G06T 7/0083* (2013.01); *A61B 6/503* (2013.01)
USPC ....................................................... 382/128

(58) Field of Classification Search
USPC ........ 382/128–132; 600/410, 420; 378/11, 15
See application file for complete search history.

(56) References Cited

U.S. PATENT DOCUMENTS 5,797,843 A * 8/1998 Fitch et al. .................... 600/437
6,188,924 B1   2/2001 Swanson et al.
(Continued)

FOREIGN PATENT DOCUMENTS

JP      H07250834 A    1/1994
JP      2002017719 A   7/2000
(Continued)

OTHER PUBLICATIONS

Crum et al ("Non-Rigid Image Registration: Theory and Practice"; Division of Imaging Sciences, The Guy's, King's and St. Thomas School of Medicine, London SE1,9RT, UK; The British Journal of Radiology, Special Issue 2004. pp. 140-153).*

(Continued)

*Primary Examiner* — Amara Abdi

(57) ABSTRACT

A system for visualizing a myocardium represented by a cardiac image comprises a resampling means and a visualizing means. The resampling means resamples the intensity levels at sampling points on a plurality of curved surfaces, each curved surface enclosing at least part of a heart cavity and zero or more of the plurality of curved surfaces and being enclosed by the remaining curved surfaces of the plurality of curved surfaces, the plurality of curved surfaces together covering a hollow region in the cardiac image, the hollow region comprising the outer cavity walls of a group of at least one heart cavity. The visualizing means is arranged for visualizing at least part of at least one of the plurality of curved surfaces, using resampled intensity levels obtained from the resampling means. The group of at least one heart cavity may be the left atrium alone. It may also be the complete heart.

15 Claims, 4 Drawing Sheets

(56) References Cited

U.S. PATENT DOCUMENTS

| | | | |
|---|---|---|---|
| 6,757,414 B1 * | 6/2004 | Turek et al. | 382/128 |
| 6,892,089 B1 * | 5/2005 | Prince et al. | 600/410 |
| 7,231,076 B2 | 6/2007 | Fu et al. | |
| 2003/0139944 A1 * | 7/2003 | Carlsen et al. | 705/2 |
| 2004/0267125 A1 * | 12/2004 | Skyba et al. | 600/443 |
| 2005/0096543 A1 * | 5/2005 | Jackson et al. | 600/441 |
| 2008/0043024 A1 * | 2/2008 | Schiwietz et al. | 345/442 |
| 2008/0107233 A1 * | 5/2008 | Sakaguchi et al. | 378/91 |
| 2008/0146932 A1 | 6/2008 | Chalana et al. | |
| 2010/0034734 A1 * | 2/2010 | O'Connor et al. | 424/1.11 |

FOREIGN PATENT DOCUMENTS

| | | |
|---|---|---|
| JP | 2007507248 A | 3/2007 |
| WO | 0134026 A1 | 5/2001 |

OTHER PUBLICATIONS

W R Crum, DPhil, T Hartkens, PhD and D L G Hill, PhD; Entitled: Non-Rigid Image Registration: Theory and Practice; Division of Imaging Sciences, The Guy's, King's and St. Thomas School of Medicine, London SE1,9RT, UK; The British Journal of Radiology, Special Issue 2004. pp. S140-S153.

Makram-Ebeid, S. et al. "Non-Rigid Image Registration using a Hierarchical Partition of Unity Finite Element Method". proceedings of the ICCV 2007 Conference, Rio de Janeiro, Oct. 14-21, 2007, p. 1-8.

Malpica, N. et al. "Myocardial Strain Analysis of Echocardiographic Sequences Using Non-Rigid Registration". Computers in Cardiology, Sep. 2004, pp. 313-316.

* cited by examiner

CARDIAC IMAGE PROCESSING AND ANALYSIS

FIELD OF THE INVENTION

The invention relates to visualizing a cardiac image. The invention also relates to motion compensation of a sequence of cardiac images. The invention also relates to strain imaging.

BACKGROUND OF THE INVENTION

The motion of cardiac tissues can be assessed by viewing medical images of the cardiac tissues, using one or more different 2D and 3D imaging modes (in particular tagged or untagged cardiac MRI, and/or different modes of ultrasound imaging). From such dynamic imaging, one can extract tissue velocity, strain and/or strain-rates. Such strain and strain rates can be visualized using parametric images, wherein the intensities associated with positions represent parameter values, such as strain or strain rate. Such parametric imaging techniques can provide valuable diagnostic information relating, among others, to hypokinesy, akinesy, diskinesy of certain part of the myocard, or myocardial asynchronism. However, the validity of this parametric imaging may depend on the image contrast and on the accuracy of the estimated motion field.

Ledesma-Carbayo, M. J. Santos, A. Kybic, J. Mahia-Casado, P. Garcia-Fernandez, M. A. Malpica, N. Perez-David, E. Desco, M.; "Myocardial strain analysis of echocardiographic sequences using nonrigid registration"; Computers in Cardiology, September 2004, pp 313-316 (hereinafter: Ledesma-Carbayo et al.), describe a way of assessing the extracted motion field accuracy. Using the extracted motion field, a motion-compensated image sequence is generated in such a manner that all images in the sequence are made similar to a selected reference frame. Usually, the reference frame is selected among end-diastolic frames.

Techniques for visualizing a cardiac image are known, for example using direct volume rendering or multi-planar reformat. However, these visualizations do not provide an efficient way to inspect the myocardium in detail.

SUMMARY OF THE INVENTION

It would be advantageous to have an improved way of visualizing a myocardium represented by a cardiac image. To better address this concern, in a first aspect of the invention a system is presented that comprises resampling means for resampling the intensity levels at sampling points on a plurality of curved surfaces, each curved surface enclosing zero or more of the plurality of curved surfaces and being enclosed by the remaining curved surfaces of the plurality of curved surfaces, the curved surfaces enclosing at least part of a heart cavity, the plurality of curved surfaces together covering a hollow region in the cardiac image, the hollow region comprising the outer cavity walls of a group of at least one heart cavity; and visualizing means for visualizing at least part of at least one of the plurality of curved surfaces, using resampled intensity levels obtained from the resampling means.

Since the curved surfaces enclose a portion of the heart cavity, and the curved surfaces enclose each other and together cover the region comprising the cavity walls, these surfaces more or less follow the shape of the heart walls as shown in the cardiac image, including the myocardium. At least some of these surfaces intersect the myocardium, and are locally approximately parallel to the myocardium. Visualization of such a surface allows inspecting a layer of the myocardium. The surfaces are distributed over the hollow region, for example equidistantly. The surfaces may form concentric shells adapted to the shape of the myocardium. The hollow region can be a three-dimensional region or volume. The hollow region may have a hole in it. For example, the hollow region comprises the outer cavity walls of the group of at least one heart cavity, wherein at least part of the at least one heart cavity is left out of the region to form the hole. For example, more than half of the heart cavity may be left out of the region to form the hole of the region. It is also possible to leave out the complete heart cavity; in that case, the inner boundary of the region coincides with the inner boundary of the cavity wall. The curved surfaces may be distributed in the hollow region. For example, the curved surfaces may take the form of concentric shells around the hole.

The group of at least one heart cavity may be the left ventricle alone, for example. In this case, the outer walls are the walls of the left ventricle. Alternatively, the group of at least one heart cavity may be the group of the four heart chambers, the outer walls being the outer walls of the heart. In the latter case, together the curved surfaces cover the region extending from epicardium to endocardium.

Adaptation means may be provided for adapting the shape of the curved surfaces to the shape of the cavity walls, making the curved surfaces have a shape similar to the cavity walls. This way, a larger part of the surface may coincide with the myocardium. When visualizing such a surface (for example in a flattened manner), a relatively large part of the myocardium, or even a complete layer of the myocardium, may be visualized.

Flattening means may be provided for unfolding and flattening a curved surface of the plurality of curved surfaces to obtain a flattened surface, wherein the sampling points on that curved surface are mapped to points on the flattened surface. The flattening means transforms (or warps) the curved surface into a substantially planar surface denoted by flattened surface. The visualization of at least part of at least one of the plurality of curved surfaces may be realized by visualizing at least part of the flattened surface. This flattened surface visualization gives a quick overview of the cardiac image around the heart.

Collecting means may be provided for combining a plurality of flattened surfaces for forming a volume image comprising a stack of the flattened surfaces. The flattened surfaces can be combined into a volume image by stacking successive flattened surfaces. Successive flattened surfaces in the stack correspond to successively larger curved surfaces.

Volume visualization means may be provided for visualizing the volume image. In principle, any volume visualization mode may be provided for visualizing the volume image, including for example slice view and maximum or minimum intensity projection (MIP).

The volume visualization means may comprise an orthoviewer. The orthoviewer, which is a viewing mode which is by itself known in the art, may allow the user to browse through the slices of the volume image, visualizing three orthogonally oriented slices of the volume image at a time.

The visualization means may be arranged for visualizing a curved surface of the plurality of curved surfaces, the curved surface being visualized in isolation from the remaining curved surfaces of the plurality of curved surfaces. This curved surface may be visualized for example in its original, curved shape, or after flattening as set forth. Such an isolated view of a curved surface may allow a close inspection of a thin shell of the myocardium.

According to an aspect of the invention, the system may be arranged for handling a time sequence of cardiac images covering at least part of a heartbeat, and the system further may comprise motion-compensating means for compensating the heart motion by transforming cardiac images of the time sequence of cardiac images to match a reference cardiac image, to obtain a sequence of motion-compensated images;

the resampling means being arranged for performing the resampling in a plurality of the motion compensated images, using the same plurality of curved surfaces.

The dataset of resampled points thus being generated can be used, for example in statistical analysis, to identify any residual motion. The dataset may be visualized dynamically using a visualization mode as described above, sequentially displaying the subsequent resampled images of the time sequence. Such visualization allows identifying residual motion. The visualization thus enables a user to assess whether the motion compensation is adequate. Motion-compensating means are known per se in the art.

The motion-compensating means may be arranged for employing a rigid or affine transformation to transform a cardiac image into a motion-compensated image. Such a rigid or affine transformation is known per se in the art. By limiting the transformation to rigid or affine transformations, most 'healthy' kinds of cardiac motion can be compensated. Pathologic, or irregular cardiac motion may not be compensated by such transformations. Asynchronies, for example, would normally not be compensated by using a rigid or affine transformation. Consequently, these pathologic or irregular cardiac motions remain in the motion-compensated images as residual motion. In combination with the resampling and visualization modes set forth, the residual motion can be identified by a user relatively efficiently, and thus the pathologic or irregular cardiac motion or asynchronies can be identified relatively efficiently.

Sequence visualization means may be provided for dynamically visualizing at least some of the resampled points corresponding to the sequence of cardiac images in their time sequential order. This visualization allows identifying residual motion.

Indicating means may be provided for enabling a user to indicate a region comprising residual motion; and the motion-compensating means may be arranged for further motion-compensating a region indicated by the user. The visualization of a cardiac image sequence as set forth allows easy spotting of residual motion. By enabling the user to identify this residual motion to the system, the system can apply further motion compensation specific to this region.

The indicating means may be arranged for further enabling the user to indicate a direction of the residual motion, the further motion-compensating means being arranged for compensating the region indicated by the user according to a direction of the residual motion indicated by the user. By using the direction, the motion compensation is improved further.

The system set forth may be incorporated into a medical workstation or imaging acquisition apparatus.

A method of visualizing a myocardium represented by a cardiac image associating intensity levels with three-dimensional points in a volume, may comprise resampling the intensity levels at sampling points on a plurality of curved surfaces, each curved surface enclosing at least part of a heart cavity and zero or more of the plurality of curved surfaces and being enclosed by the remaining curved surfaces of the plurality of curved surfaces, the plurality of curved surfaces together covering a hollow region in the cardiac image, the hollow region comprising the outer cavity walls of a group of at least one heart cavity; and visualizing at least part of at least one of the plurality of curved surfaces, using resampled intensity levels obtained from the resampling means.

A computer program product may be provided comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the system, of the method, of the image acquisition apparatus, of the workstation, and/or of the computer program product, which correspond to the described modifications and variations of the system or the method, can be carried out by a person skilled in the art on the basis of the present description.

A person skilled in the art will appreciate that the method may be applied to multidimensional image data, e.g., to 2-dimensional (2-D), 3-dimensional (3-D) or 4-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined by the independent claims. Advantageous embodiments are defined in the dependent claims.

BRIEF DESCRIPTION OF THE DRAWINGS

These and other aspects of the invention will be further elucidated and described with reference to the drawing, in which.

DETAILED DESCRIPTION OF EMBODIMENTS

Cardiac tissue motion fields can be extracted, for example, directly from the imaging mode (Doppler US or specialized MRI modes) or by using a rigid or non-rigid registration technique, for example as described in Ledesma-Carbayo et al. However, several difficulties have to be solved in order to correct and assess the validity of the estimated motion-field.

The acquired image contrast may be low in the region where motion has to be assessed. Examining the motion-compensated image sequence may be a tedious and lengthy task when using 3D time sequences (4D visualization).

Figure 1:
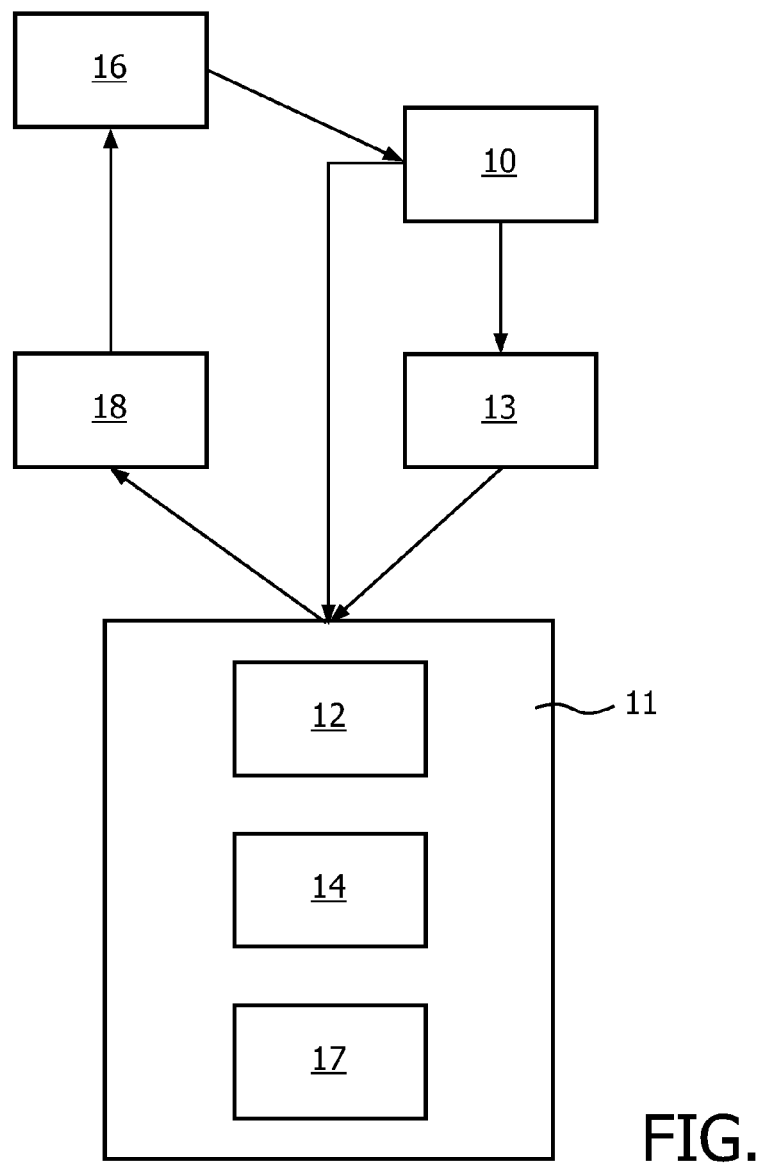
FIG. 1 illustrates a system for visualizing a myocardium represented by a cardiac image.

FIG. 1 illustrates a system for visualizing a myocardium represented by a cardiac image associating intensity levels with three-dimensional points in a volume. Such a cardiac image is known as a volumetric cardiac image. The system may comprise a computer system including a central processor unit, memory, and storage means, as known in the art. Some or all of the means and modules described herein can be implemented in software.

Resampling means 10 may be provided for resampling the intensity levels at sampling points on a plurality of curved surfaces. Each curved surface encloses at least part of a heart cavity and zero or more of the plurality of curved surfaces and is enclosed by the remaining curved surfaces of the plurality of curved surfaces. The plurality of curved surfaces together cover a hollow region in the cardiac image. The hollow region may comprise the outer cavity walls of a group of at least one heart cavity. For example, the region has the shape of a shell around the heart cavity or heart cavities, although the region may partly overlap the heart cavity or heart cavities.

Visualizing means 11 may be provided for visualizing at least part of at least one of the plurality of curved surfaces, using resampled intensity levels obtained from the resampling means. The visualizing means 11 may comprise flattening means 12 for unfolding and flattening a curved surface of the plurality of curved surfaces to obtain a flattened surface, wherein the sampling points on that curved surface are mapped to points on the flattened surface. The system may comprise collecting means 13 for combining a plurality of flattened surfaces for forming a volume image comprising a stack of the flattened surfaces. This will be elaborated hereinafter. The visualizing means 11 may comprise volume visualization means 14 for visualizing the volume image, for example using an orthoviewer.

The visualization means 14 may be arranged for visualizing a curved surface of the plurality of curved surfaces, the curved surface being visualized in isolation from the remaining curved surfaces of the plurality of curved surfaces. This happens in an orthoviewer, for example.

The system may be arranged for handling a time sequence of cardiac images covering at least part of a heart beat. This sequence of images may be received via an input, for example a network connection, or may be stored on a local memory. The system may further comprise motion-compensating means 16 for compensating the heart motion by transforming cardiac images of the time sequence of cardiac images to match a reference cardiac image, to obtain a sequence of motion-compensated images. The resampling means 10 may be arranged for performing the resampling in a plurality of the motion-compensated images, using the same plurality of curved surfaces. So, the sequential motion-compensated images are sampled at the same points. This way, a movie can be created of the intensities on one of the curved surfaces, for example. Using collecting means 13, it is also possible to collect the resampled data of the sequential compensated images to form a sequence of volume images. This sequence can be dynamically visualized using a volume viewer, such as an orthoviewer.

The motion compensating means 16 may be arranged for employing a rigid or affine transformation to transform a cardiac image into a motion-compensated image. Visualizing the motion-compensated images made using this rigid or affine transformation allows a viewer to detect pathologies or asynchronies.

The visualization means 11 may comprise sequence visualization means 17 for dynamically visualizing at least some of the resampled points corresponding to the sequence of cardiac images in their time sequential order.

Indicating means 18 may be provided for enabling a user to indicate a region comprising residual motion. The motion-compensating means 16 may be arranged for further motion-compensating a region indicated by the user.

The indicating means 18 may be arranged for further enabling the user to indicate a direction of the residual motion, the motion-compensating means 16 being arranged for compensating the region indicated by the user according to a direction of the residual motion indicated by the user.

The system set forth may be included in a medical workstation, for example. The system may also be included in a medical image acquisition apparatus.

Figure 2:
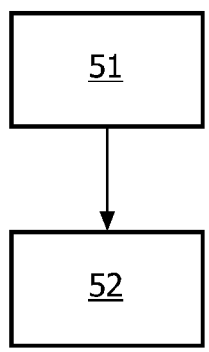
FIG. 2 illustrates a method of visualizing a myocardium represented by a cardiac image.

FIG. 2 illustrates a method of visualizing a myocardium represented by a cardiac image associating intensity levels with three-dimensional points in a volume. The method comprises, in step 51, resampling the intensity levels at sampling points on a plurality of curved surfaces, each curved surface enclosing at least part of a heart cavity and zero or more of the plurality of curved surfaces and being enclosed by the remaining curved surfaces of the plurality of curved surfaces, the plurality of curved surfaces together covering a hollow region in the cardiac image, the hollow region comprising the outer cavity walls of a group of at least one heart cavity. The method further comprises, in step 52, visualizing at least part of at least one of the plurality of curved surfaces, using resampled intensity levels obtained from the resampling means.

The visualization used for motion-accuracy assessment and for parametric imaging may be made adaptable to the heart shape. This is particularly the case if a segmentation of the heart is available for the reference frame.

Visualization techniques may be applied for enabling a user to assess the quality or reliability of the estimated tissue-motion field. Moreover, regions where this estimation is doubtful may be automatically highlighted. An interactive procedure may be employed for correcting tissue-motion fields within compact regions or volumes of interest (ROI or VOI, respectively) and for locally improving the motion field within the ROI/VOI. Using a segmentation of the heart, the visualization geometry can be adapted to the heart morphology. However, this is not a limitation. For example, a model of the heart may be used for adapting the visualization geometry.

Figure 3:
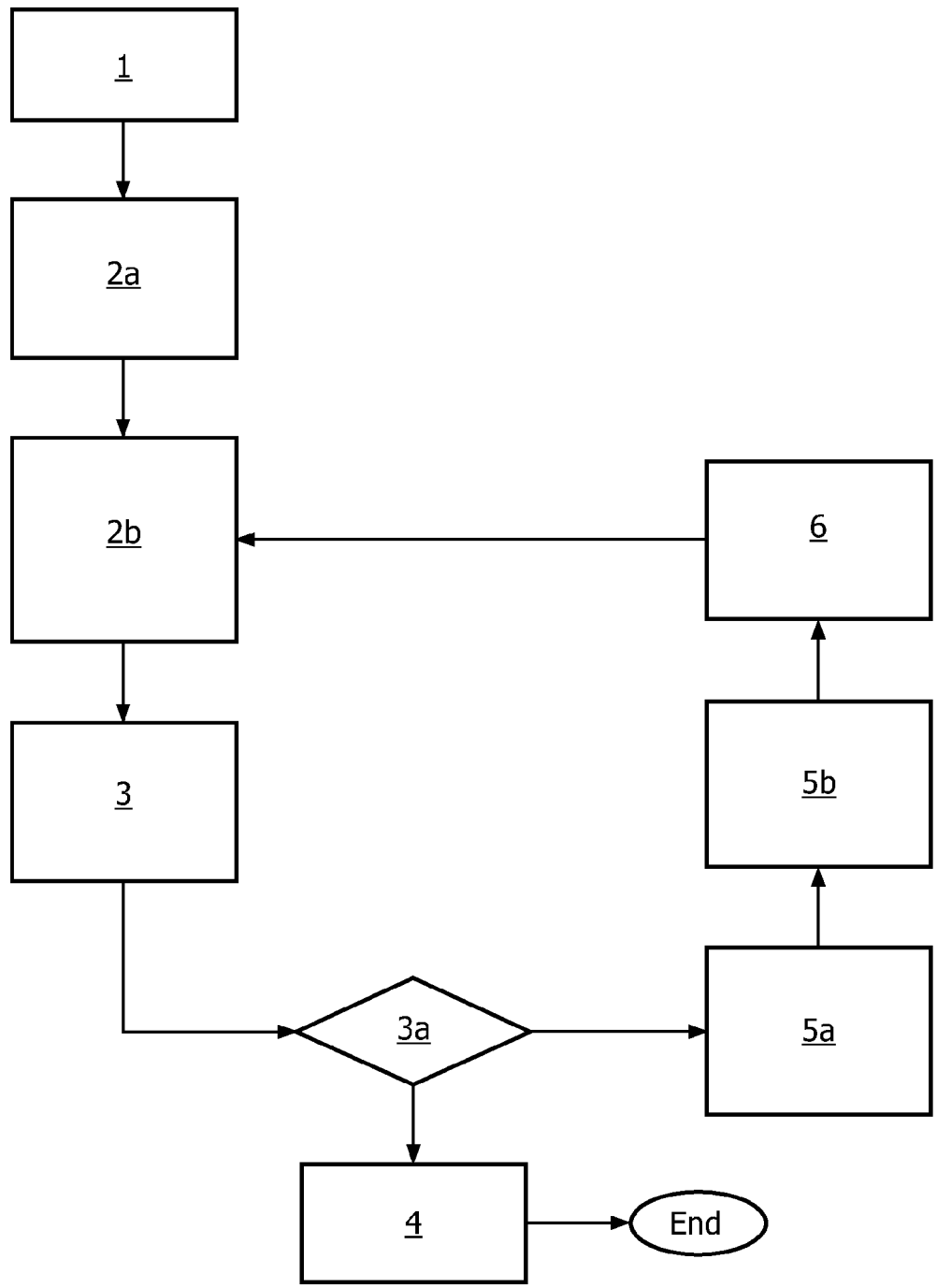
FIG. 3 illustrates a process of validating and improving a motion field.

FIG. 3 illustrates a process of validating and improving a motion field. In step 1, acquisition of a cardiac image sequence may be performed and saved. For example, a 3D ultrasound image acquisition takes place, or a cardiac CT image acquisition.

In step 2a, motion fields may be estimated. In step 2b, a motion-compensated image sequence may be generated using the estimated non-rigid motion. Any non-rigid image registration algorithm which is capable of estimating and correcting a motion field in a specified ROI/VOI may be used. A suitable registration algorithm is disclosed in S. Makram-Ebeid and O. Somphone, "Non-Rigid Image Registration using a Hierarchical Partition of Unity Finite Element Method"; Proceedings of the ICCV 2007 Conference, Rio de Janeiro, Oct. 14-21, 2007 (referred to hereinafter as: Makram-Ebeid et al.). The compensation may be performed in such a manner that all images in the sequence are made similar to a selected frame (typically an End-Diastolic Frame), in other words, the portions of the heart which have moved are "warped" to their corresponding position in the reference image.

In step 3, dynamic visualization of the motion-compensated images may be used to enable a user to interactively examine the anatomically relevant parts to see whether heart tissues appear immobile. Additionally or alternatively, apparent motion may be detected by computing the local spatial and/or temporal image variance. Spatial variance may be evaluated within a specified neighborhood of b voxels from each image element where b can be 3 to 5 for example. Temporal variance likewise may be calculated within the current, the immediately preceding and the immediately succeeding time frame or time frames. Regions of residual apparent motion may be those for which the time variance of image intensity is larger than its spatial variance. Those regions may be automatically highlighted in the dynamic visualization. A segmentation of the heart in the reference frame can be advantageously used in order to define a coordinate system adapted to the heart anatomy. Image data may be reformatted and visualized using this coordinate system.

Upon user request, motion, strain and/or strain-rate parameters can be extracted from the evaluated motion field and may be visualized using parametric imaging procedures. Strain and/or motion synchronies or asynchronies may also be quantitatively assessed and displayed. Techniques for quantitatively assessing strain and/or motion synchronies are known in the art.

Illustrated in step 3a, confidence in the resulting parametric imaging can be asserted if image quality is sufficient and there is substantially no apparent motion in the compensated image sequence. In case confidence has been asserted, the user can decide to visualize the parametric images for diagnostic purposes (in step 4). Otherwise, the process may continue in step 5a.

Residual motion highlighted in step 3 may be caused by poorly contrasted image regions. Such residual motion may be removed in a process which involves user interactions. In step 5a, the user may indicate the region where motion estimation needs correction, for example by defining a spatial ROI/VOI covering the region. The direction in which motion vectors need an update may also be indicated by the user (transversal and/or longitudinal and/or circumferential). The ROI/VOI allows the definition of a fuzzy window function within which the motion field corrections may be recomputed (in step 5b). The motion field corrections in the indicated region may be recomputed using techniques disclosed in Makram-Ebeid et al. In step 6, the local correction is then applied to the previous estimation of the motion field, to obtain an improved overall motion field.

The process may iteratively proceed to steps 2b, 3, 3a, 5a, 5b, and 6. A new acquisition (step 1) may be performed if it is decided that the image quality is unsuitable or if the above correction procedure does not provide an acceptable result.

Figure 4A:
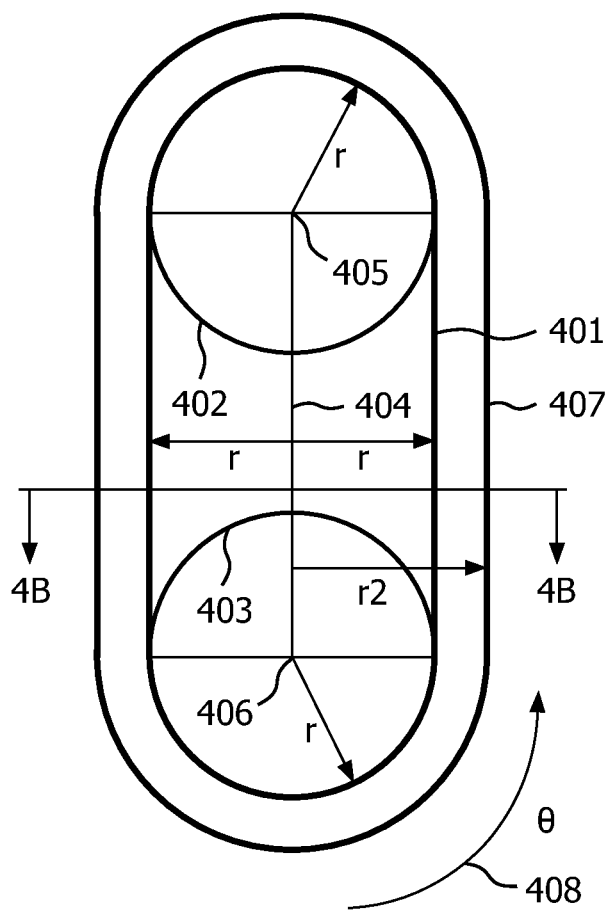
FIG. 4 illustrates a curved surface.
Figure 4B:
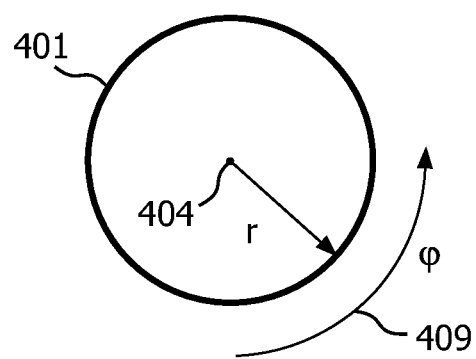

FIG. 4 illustrates a coordinate system which allows following the anatomical shape of the heart or of a heart chamber such as the left ventricle. In the Figures, the same items have in general been labeled with the same reference numerals. FIG. 4A shows a cross sectional view of a curved surface 401. However, this curved surface is only an example, not a limitation. Curved surface 401 is a closed surface. However, this is not a limitation. For example, a portion of the curved surface 401 may be used. Moreover, the Figure illustrates axis 404, extending from point 405 to point 406, approximately parallel to a line connecting the apex and the base of the heart. Parameter value r (illustrated at several places in FIG. 4) represents the distance from the axis 404. The curved surface 401 has the same distance r from axis 404 everywhere on the curved surface 401. Moreover, a parameter .theta. represents the position on the curved surface 401 around the axis 404, in the direction indicated by arrow 408. For example, this could be expressed in millimeters distance along this curve 404 from a predefined reference point on this curve 401, in counterclockwise direction. Other units can also be used for this parameter .theta. FIG. 4B illustrates another cross sectional view of the curved surface 401, the orientation of the cross sectional view of FIG. 4B is illustrated in FIG. 4A. Parameter Φ represents the angular position around the axis (in degrees for example, starting from a predetermined reference angular position), as indicated by arrow 409. The length, position, and orientation of axis 404, as well as the radius r may be selected such that the curved surface 401 more or less corresponds to the curved surface 401, and more particularly such that, given the axis 404 thus selected, a minimal radius r can be selected, having a first curved surface 401 associated therewith, and a maximal radius r2 can be selected, having a second curved surface 407 associated therewith, such that the myocardium of a heart chamber (or the outer walls of the entire heart, as desired) is completely contained in between the two curved surfaces 401 and 407.

It is possible to resample all or part of a cardiac image, using the above introduced parameters θ, φ, and r, at regular intervals, for example on regular grid points or rectangular grid points. This is a way to "unfold" the surface. The same co-ordinate system may be used for all frames in a temporal image sequence. In particular if the temporal image sequence comprises motion-compensated images, a relatively narrow band between the first curved surface 401 and the second curved surface 407 can be realized, while capturing the myocardium in each image. The resampling may result in a new rectangular volume image, wherein the parameters θ, φ, and r form a normal, rectangular three-dimensional coordinate space. This rectangular volume may be viewed in an orthoviewer for example. A temporal sequence of motion-compensated, resampled images may be displayed in this orthoviewer. The user may indicate in this orthoviewer a Region Of Interest (ROI) where the motion estimation should be improved. Using the coordinate system, this region of interest can be identified in the original (motion-compensated) cardiac images, which enables the motion compensation to be improved in that region of interest.

The curved surface 401 may be adapted to the shape of the heart, in particular the shape of the heart walls, or myocardium. This adaptation may be based on a segmentation of the heart. A technique to obtain such a surface which is adapted to the shape of the heart is adaptive shape models. Adaptive shape models are known in the art.

Figure 5:
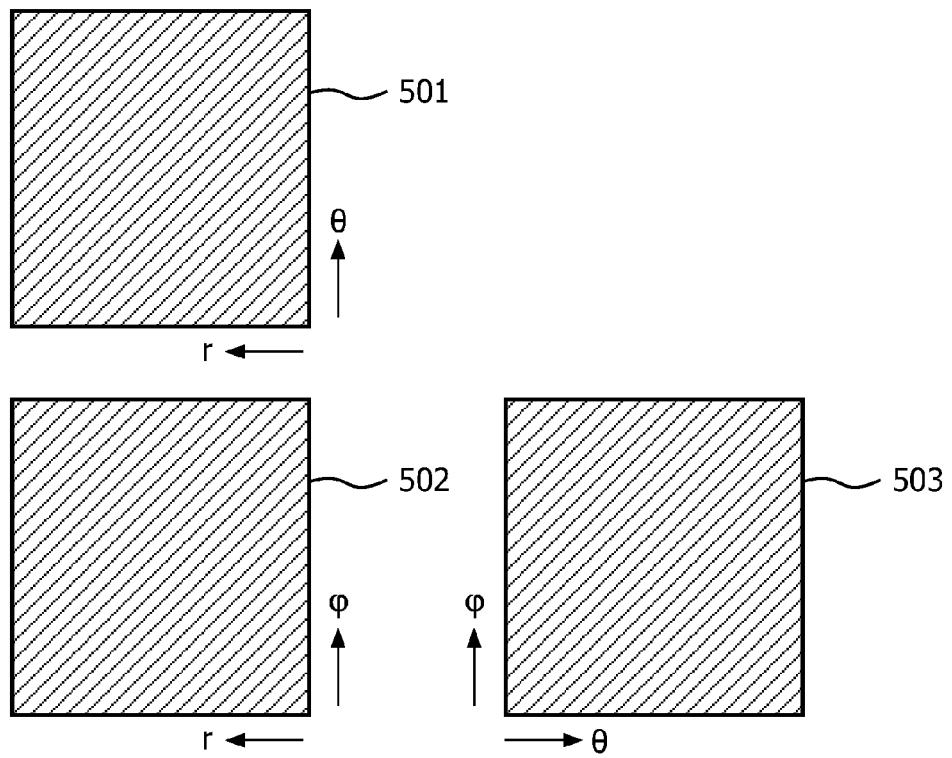
FIG. 5 illustrates three quadrants of an orthoviewer.

FIG. 5 illustrates an orthoviewer. Three quadrants are displayed. The quadrant 501 shows a slice of the resampled volume along r and the θ axis. φ may be varied to view different slices. The quadrant 502 shows a slice of the resampled volume along r and the φ axis. θ may be varied to view different slices. The quadrant 503 shows a slice of the resampled volume along θ and the φ axis. r may be varied to view different slices. The user may select which slices he wishes to view. The top right quadrant may be used for a different visualization mode, for example. The orthoviewer is a way of visualizing flattened surfaces.

As indicated above, the surfaces may be adapted to the shape of the heart walls. In such a case, the region of the image displayed in the quadrants of the orthoviewer of FIG. 5 follow the region covered by the surfaces; in particular the range of values of r that are displayed may vary depending on the parameters θ and φ. The smallest value in the range may correspond to the surface closest to the center of the heart (or the center of a heart cavity, as the case may be), and the largest value in the range may correspond to the surface most remote from this center.

Figure 6:
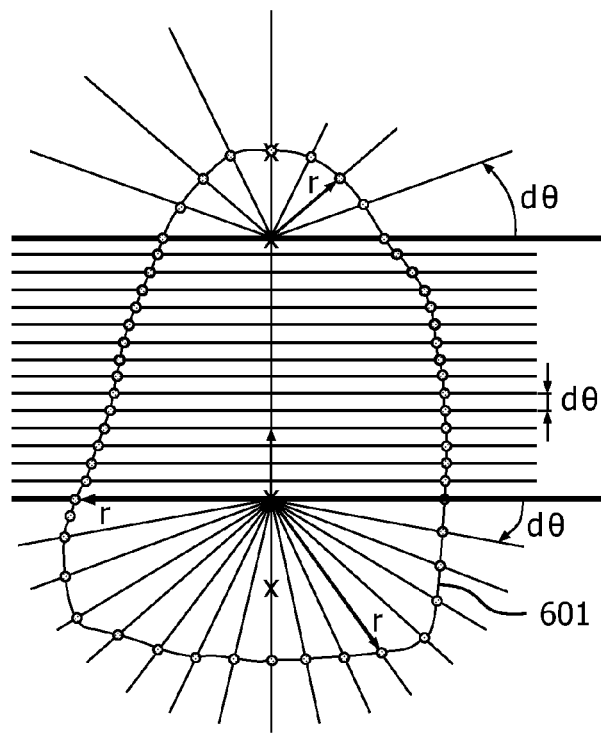
FIG. 6 illustrates an adapted curved surface adapted to the shape of the heart.

FIG. 6 shows an intersection of a curved surface 601 which has been adapted to the shape of the heart. dθ denotes the meaning of a step along the θ axis. A few examples of the radius r have also been indicated in the Figure.

The techniques set forth may be used for example in an echographic system on-cart and/or off-cart in a deported workstation. The same method can be applied for a visualization or acquisition cardiac imaging workstation, for example an MRI cardiac imaging workstation.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or stored in one or more files that may be linked statically or dynamically. Another embodiment relating to a computer program product comprises computer executable instructions corresponding to each of the means of at least one of the systems and/or products set forth. These instructions may be subdivided into subroutines and/or stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in such a signal, the carrier may be constituted by such a cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for visualizing a myocardium represented by a cardiac image associating intensity levels with three-dimensional points in a volume, comprising
    resampling means for resampling the intensity levels at sampling points on a plurality of curved surfaces, each curved surface enclosing zero or more of the plurality of curved surfaces and being enclosed by the remaining curved surfaces of the plurality of curved surfaces, the curved surfaces enclosing at least part of a heart cavity, the plurality of curved surfaces together covering a hollow region in the cardiac image, the hollow region comprising the outer cavity walls of at least one heart cavity; and
    visualizing means for visualizing at least part of at least one of the plurality of curved surfaces, using resampled intensity levels obtained from the resampling means.

2. The system according to claim 1, wherein the at least one heart cavity being the left ventricle, the outer walls being the walls of the left ventricle.

3. The system according to claim 1, further comprising adaptation means for adapting the shape of the curved surfaces to the shape of the cavity walls, causing the curved surfaces to have a shape similar to the cavity walls.

4. The system according to claim 1, wherein the visualizing means comprising flattening means for unfolding and flattening a curved surface of the plurality of curved surfaces to obtain a flattened surface, wherein the sampling points on that curved surface are mapped to points on the flattened surface.

5. The system according to claim 4, further comprising collecting means for combining a plurality of flattened surfaces for forming a volume image comprising a stack of the flattened surfaces.

6. The system according to claim 5, wherein the visualizing means comprising volume visualization means for visualizing the volume image.

7. The system according to claim 6, wherein the volume visualization means comprising an orthoviewer.

8. The system according to claim 1, arranged for handling a time sequence of cardiac images covering at least part of a heartbeat, the system further comprising
    motion-compensating means for compensating the heart motion by transforming cardiac images of the time sequence of cardiac images to match a reference cardiac image, to obtain a sequence of motion-compensated images;
    the resampling means being arranged for performing the resampling in a plurality of the motion-compensated images, using the same plurality of curved surfaces.

9. The system according to claim 8, wherein the motion-compensating means being arranged for employing a rigid or affine transformation to transform a cardiac image into a motion-compensated image.

10. The system according to claim 8, wherein the visualization means comprising sequence visualization means for dynamically visualizing at least some of the resampled points corresponding to the sequence of cardiac images in their time-sequential order.

11. The system according to claim 10, further comprising
    indicating means for enabling a user to indicate a region comprising residual motion; and
    the motion-compensating means being arranged for further motion compensating a region indicated by the user.

12. The system according to claim 11, wherein the indicating means being arranged for further enabling the user to indicate a direction of the residual motion, the motion-compensating means being arranged for compensating the region indicated by the user according to a direction of the residual motion indicated by the user.

13. A medical workstation comprising the system according to claim 1.

14. A method of visualizing a myocardium represented by a cardiac image associating intensity levels with three-dimensional points in a volume, comprising
  resampling the intensity levels at sampling points on a plurality of curved surfaces, each curved surface enclosing zero or more of the plurality of curved surfaces and being enclosed by the remaining curved surfaces of the plurality of curved surfaces, the curved surfaces enclosing at least part of a heart cavity, the plurality of curved surfaces together covering a hollow region in the cardiac image, the hollow region comprising the outer cavity walls of at least one heart cavity; and
  visualizing at least part of at least one of the plurality of curved surfaces, using resampled intensity levels obtained from the resampling means.

15. A non-transitory computer-readable medium storing a computer program product comprising instructions for causing a processor system to perform the method according to claim 14.

\* \* \* \* \*